(12) United States Patent
Tamaoki et al.

(10) Patent No.: US 6,183,666 B1
(45) Date of Patent: Feb. 6, 2001

(54) CHOLESTERYL COMPOUND AND REWRITABLE FULL-COLOR THERMOSENSITIVE RECORDING MATERIAL

(75) Inventors: Nobuyuki Tamaoki; Hiroo Matsuda, both of c/o Agency of Industrial Science And Technology, National Institute of Materials and Chemical Research, 1-1, Higashi, Tsukuba-shi, Ibaraki-ken, 305-0046; Yoshishige Kida, Osaka, all of (JP)

(73) Assignees: Ricoh Company, Ltd., Tokyo; Okamura Oil Mill, Ltd., Kashiwara; Nobuyuki Tamaoki, Tsukuba; Hiroo Matsuda, Tsukuba; Director- General of Agency of Industrial and Science and Technology, Tsukuba, all of (JP)

( * ) Notice: Under 35 U.S.C. 154(b), the term of this patent shall be extended for 0 days.

(21) Appl. No.: 09/363,646

(22) Filed: Jul. 30, 1999

(30) Foreign Application Priority Data

Jul. 31, 1998 (JP) .................................................. 10-217596

(51) Int. Cl.[7] .............................. C09K 19/36; G03C 1/00; C07J 9/00
(52) U.S. Cl. ................................ 252/299.7; 349/2; 359/3; 430/20; 552/544
(58) Field of Search ............................ 252/299.7; 430/20, 430/19; 349/2, 115, 176; 359/3; 428/694; 560/6; 552/544; 503/221

(56) References Cited

U.S. PATENT DOCUMENTS

| | | | | |
|---|---|---|---|---|
| 4,933,243 | * | 6/1990 | Hara et al. | 430/20 |
| 5,364,829 | * | 11/1994 | Kishimoto et al. | 503/201 |
| 5,780,387 | * | 7/1998 | Harada | 503/226 |
| 6,103,431 | * | 8/2000 | Tamaoki et al. | 430/20 |

FOREIGN PATENT DOCUMENTS 6-273707 * 9/1994 (JP) .
11-24027 * 1/1999 (JP) .

* cited by examiner

*Primary Examiner*—Shean C. Wu
(74) *Attorney, Agent, or Firm*—Oblon, Spivak, McCleland, Maier & Neustadt, P.C.

(57) ABSTRACT

A cholesteryl compound has formula (1), and a rewritable full-color thermosensitive recording material contains the above-mentioned cholesteryl compound of formula (1):

$$YO\text{—}CO(CH_2)_n\text{—}A\text{—}(CH_2)_n CO\text{—}OY \qquad (1)$$

wherein A is a 1,5-hexadienylene group represented by the formula $-C(R)=CHCH_2CH_2CH=C(R)-$, in which R is a hydrogen atom or methyl group; Y is a cholesterol residue obtained by removing a hydroxyl group from cholesterol; and n is an integer of 5 to 7.

2 Claims, No Drawings

CHOLESTERYL COMPOUND AND REWRITABLE FULL-COLOR THERMOSENSITIVE RECORDING MATERIAL

BACKGROUND OF THE INVENTION

1. Field of the Invention

The present invention relates to a cholesteryl compound with liquid crystalline properties, and a rewritable full-color thermosensitive recording material comprising the above-mentioned cholesteryl compound.

2. Discussion of Background

Color photographs and photocopiers are known as recording materials capable of recording a full-color image, but not capable of rewriting the recorded image. On the other hand, there are known recording materials capable of rewriting the recorded information, but not capable of achieving full-color recording, for example, a thermosensitive recording material comprising a long-chain alkyl carboxylic acid derivative such as behenic acid; an optical recording material comprising a photochromic compound such as a spiropyran derivative; and a magnetic and magneto-optical memory material.

As shown in the above-mentioned conventional recording materials, full-color recording and rewritable recording are not achieved at the same time.

Some image display materials, for example, television devices and liquid crystal devices can display full-color changeable images. However, these image display materials cannot be made compact, for instance, into a thin card that can be kept in a wallet. In addition, the color image displayed in the above-mentioned display materials cannot be stably maintained without a power source. For these reasons, the above-mentioned image display materials cannot be used as recording materials.

Achievement of rewritable full-color recording using liquid crystalline compounds is reported (N. Tamaoki et al. Advanced Materials 9 (14), 1102 (1997)). In this case, however, the peak of the reflection band of the reflection spectrum is, at most, 610 nm on the long wavelength side, so that it is difficult for the above-mentioned liquid crystalline compounds to assume a red color.

SUMMARY OF THE INVENTION

Accordingly, a first object of the present invention is to provide a liquid crystalline compound that is useful as a rewritable full-color thermosensitive recording material.

A second object of the present invention is to provide a rewritable full-color thermosensitive recording material using the above-mentioned liquid crystalline compound.

The above-mentioned first object of the present invention can be achieved by a cholesteryl compound of the following formula (1):

YO—CO(CH$_2$)$_n$—A—(CH$_2$)$_n$CO—OY  (1)

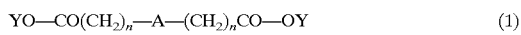

wherein A is a 1,5-hexadienylene group represented by the formula —C(R)=CHCH$_2$CH$_2$CH=C(R)—, in which R is a hydrogen atom or methyl group; Y is a cholesterol residue obtained by removing a hydroxyl group from cholesterol; and n is an integer of 5 to 7.

The second object of the present invention can be achieved by a rewritable full-color thermosensitive recording material comprising a cholesteryl compound of the following formula (1):

YO—CO(CH$_2$)$_n$—A—(CH$_2$)$_n$CO—OY  (1)

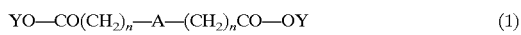

wherein A is a 1,5-hexadienylene group represented by the formula —C(R)=CHCH$_2$CH$_2$CH=C(R)—, in which R is a hydrogen atom or methyl group; Y is a cholesterol residue obtained by removing a hydroxyl group from cholesterol; and n is an integer of 5 to 7.

DESCRIPTION OF THE PREFERRED EMBODIMENTS

The cholesteryl compound of formula (1) according to the present invention is obtained by a condensation reaction of a long-chain dibasic acid comprising a 1,5-hexadienylene group (hereinafter simply referred to as a long-chain dibasic acid) and cholesterol.

The above-mentioned long-chain dibasic acid, which is represented by the following formula (2), has 18 to 24 carbon atoms in its molecule.

HOOC—(CH$_2$)$_n$—A—(CH$_2$)$_n$—COOH  (2)

wherein A is a 1,5-hexadienylene group, and n is an integer of 5 to 7.

To be more specific, the moiety A in the above formula (2), that is, the 1,5-hexadienylene group is represented by the following formula (3):

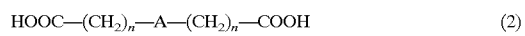

(3)

wherein R is a hydrogen atom or methyl group.

The previously mentioned long-chain dibasic acid is conventionally known, and can be synthesized by the method of Kida et al., as reported in j. Jpn. Oil Chem. Soc. (YUKAGAKU) Kida et al., 41,385 (1992).

According to the above-mentioned synthesis method, cycloalkanones are treated with hydrogen peroxide in methanol, whereby hydroperoxides with methoxy group are obtained. This reaction is shown by the following reaction scheme (4):

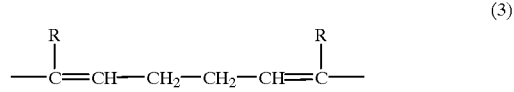

(4)

Thereafter, a mixture of the above obtained hydroperoxide and 1,3-butadiene or 2-methyl-1,3-butadiene is allowed to react with iron(II) salts, thereby providing a long-chain dibasic acid ester comprising a 1,5-hexadienylene group. The thus obtained ester is subjected to saponification, whereby the long-chain dibasic acid of formula (2) is obtained.

In the condensation reaction of the long-chain dibasic acid of formula (2) and cholesterol, 2 to 4 moles, preferably 2 to 3 moles of the cholesterol may be allowed to react with one mole of the long-chain dibasic acid.

The above-mentioned condensation reaction is carried out in the presence of dicyclohexyl carbodiimide and 4-dimethylaminopyridine in a reaction solvent such as methylene chloride at room temperature for approximately 12 hours, with stirring.

In this case, dicyclohexyl carbodiimide has a function of activating the long-chain dibasic acid and may be employed in an amount of 1 to 2 moles with respect to one mole of cholesterol. 4-dimethylaminopyridine, which serves as a condensation catalyst, may be employed in an amount of 0.1 to 0.2 moles with respect to 1 mole of cholesterol.

The cholesteryl compound represented by formula (1) has liquid crystalline properties, and is capable of reproducing iridescent colors that can be selected from the whole visible region according to the temperature to which the compound is heated. Namely, the cholesteryl compound of the present invention assumes a dark red color at 110° C. In the measurement of the reflection spectrum, it is confirmed that the cholesteryl compound assuming a red color reflects the light with a peak reflection band at 750 nm. When the above-mentioned cholesteryl compound of the present invention is heated to 112° C., 113° C., 117° C., 124° C. and 132° C. and maintained at the respective temperatures, it is confirmed by the reflection spectra of the compound that the peak reflection band is respectively at 660, 570, 490, 450 and 400 nm.

Furthermore, the cholesteryl compound according to the present invention can be used for a full-color thermosensitive recording (and displaying) material because the colors of the cholesteryl compound can be fixed.

When the cholesteryl compound of the present invention is used for the full-color thermosensitive recording material, the cholesteryl compound may be, for example, interposed between two supports, thereby providing a recording medium. In this case, a thin glass plate, a polymeric film and a metal plate are usable as the support. At least one of the two supports is required to have transparency capable of transmitting at least a portion of the light therethrough. Further, it is desirable that one of the supports have light absorbing properties when information is recorded in the recording medium and erased therefrom using the application of light.

When the recording medium is fabricated by interposing the cholesteryl compound of the present invention between two supports, the cholesteryl compound (or a mixture comprising the cholesteryl compound) is first heated to such a degree that the cholesteryl compound can assume a fused phase or liquid crystalline phase, and the cholesteryl compound in such a state is coated on one support. Thereafter the other support is overlaid thereon. Alternatively, two supports are disposed in parallel, and the cholesteryl compound in the above-mentioned state is sucked into the gap between the two supports under reduced pressure or by means of capillarity. In this case, the gap between the two supports is not particularly limited, but preferably in the range of several microns to approximately 100 μm.

Further, the cholesteryl compound of the present invention is not always necessarily held between the two supports, as mentioned above. Namely, the cholesteryl compound may be dispersed in a polymer to provide a polymer-dispersed liquid crystal. In addition, the cholesteryl compound may be used in microcapsule form when coated on the support.

Information can be recorded in the full-color thermosensitive recording material of the present invention and displayed thereon by the application of heat to the recording material. The various heating systems can be employed such as a thermal head, heat-application roll, and laser beam. For controlling the temperature of the liquid crystalline cholesteryl compound, the temperature of the thermal head or heat-application roll is adjusted, or the intensity or spot size of the laser beam is controlled. Or, after the entire surface of the recording material is heated to a predetermined temperature, the recording material may be cooled to a particular temperature by contact with an image-bearing flat metal plate or rubber plate.

In addition, the colors of the cholesteryl compound can be fixed by rapidly cooling the cholesteryl compound to the glass transition temperature or less after heating. To cool the cholesteryl compound, this cholesteryl compound may be placed in a cooled atmosphere, for example, using a refrigerant, or brought into contact with a head which has been cooled to a predetermined temperature.

The cholesteryl compound of formula (1) can be used alone or in combination with other compounds when applied to the full-color thermosensitive recording material of the present invention. For instance, liquid crystalline compounds such as monocholesteryl ester and dicholesteryl ester, and cholesterol may be used together with the cholesteryl compound of formula (1).

Other features of this invention will become apparent in the course of the following description of exemplary embodiments, which are given for illustration of the invention and are not intended to be limiting thereof.

EXAMPLE 1

Synthesis of Dicholesteryl 8,12-eicosadienedioate 3.62 g (0.01 mol) of 8,12-eicosadienedioic acid (represented by the previously mentioned formula (2), wherein n=6, and A is a 1,5-hexadienylene group represented by the formula (3) in which R=H), 8.50 g (0.022 mol) of cholesterol, and 0.51 g (0.0025 mol) of dicyclohexyl carbodiimide were dissolved in 100 ml of ethylene chloride. The above prepared reaction mixture was stirred for 20 hours at room temperature with the addition of 0.2 g of 4-dimethylaminopyridine serving as a condensation catalyst. The thus prepared reaction product was filtered off, and isolated by column chromatography on silica gel using ethylene chloride as a developing solvent. Thus, 7.56 g (0.0068 mol) of a cholesteryl ester (dicholesteryl 8,12-eicosadienedioate) was obtained. The melting point of this cholesteryl ester was 136° C.

EXAMPLE 2

The cholesteryl ester synthesized in Example 1, that is, dicholesteryl 8,12-eicosadienedioate, was held between two glass plates with a thickness of 0.18 mm, so that a thermosensitive recording material was provided. The thickness of the cholesteryl ester layer interposed between the glass plates was adjusted to 20 μm by heating the above-mentioned recording material to 150° C. so as to fuse the cholesteryl ester.

Thereafter, the recording material was placed on a hot plate at 111° C., whereby the recording material entirely assumed a dark red color. Then, the recording material was promptly immersed in ice water, so that the cholesteryl ester for use in the recording material was solidified, with the dark red color being fixed as it is.

It was confirmed by the measurement of the reflection spectrum that the aforementioned solid cholesteryl ester selectively reflected light having a peak reflection band at 750 nm.

Similarly, the recording material was heated to various temperatures with the hot plate being maintained at 112° C., 113° C., 117° C., 124° C. and 132° C., followed by rapid cooling to fix the produced respective colors. The peaks reflection bands of the reflection spectra were respectively fixed at 660, 570, 490, 450 and 400 nm. Those colors were red, green and blue.

EXAMPLE 3

The cholesteryl ester synthesized in Example 1, that is, dicholesteryl 8,12-eicosadienedioate, was held between two glass plates with a thickness of 0.18 mm, so that a thermosensitive recording material was provided. The thickness of the cholesteryl ester layer interposed between the glass plates was adjusted to 20 μm by heating the above-mentioned recording material to 150° C. so as to fuse the cholesteryl ester.

Thereafter, the recording material was placed on a hot plate at 140° C., whereby the recording material entirely assumed a blue color. Then, a rubber stamp carrying character images thereon was overlaid on the recording material in such a way that the embossed character images came in contact with the recording material so as to cool the recording material imagewise. Two seconds later, the recording material was promptly immersed in ice water. As a result, a color image composed of a blue background portion and green character image portions was obtained. Even after the color image bearing recording material was returned to room temperature, the above-mentioned color image was stable.

EXAMPLE 4

The cholesteryl ester synthesized in Example 1, that is, dicholesteryl 8,12-eicosadienedioate, was held between two glass plates with a thickness of 0.18 mm, so that a thermosensitive recording material was provided. The thickness of the cholesteryl ester layer interposed between the glass plates was adjusted to 20 μm by heating the above-mentioned recording material to 150° C. so as to fuse the cholesteryl ester.

In the above-mentioned recording material, one of the glass plates was surface-treated by applying a black coating to one surface of the glass plate. When preparing the recording material, the glass plate was disposed in such a configuration that the black surface was brought into contact with the cholesteryl ester layer.

The recording material was placed on a hot plate at 111° C., whereby the recording material entirely assumed a red color. Then, optical second harmonics (532 nm) of an Nd:YAG laser was applied to the recording material from the side of the glass plate which did not have the black coating, and the recording material was immersed in ice water. As a result, the laser-applied portion changed to an orange color and the orange color was fixed.

EXAMPLE 5

The cholesteryl ester synthesized in Example 1, that is, dicholesteryl 8,12-eicosadienedioate, was held between two glass plates with a thickness of 0.18 mm, so that a thermosensitive recording material was provided. The thickness of the cholesteryl ester layer interposed between the glass plates was adjusted to 20 μm by heating the above-mentioned recording material to 150° C. so as to fuse the cholesteryl ester.

Thereafter, the recording material was placed on a ceramic plate at room temperature for gradual cooling. The cholesteryl ester layer turned into a white crystallite film.

Then, a line was drawn on the recording material with a thermal head by rubbing the thermal head, of which the tip portion was set at 140° C. or more on the glass plate of the recording material. Once the line image appeared to be transparent, the line image portion gradually changed to a blue color. The moment the color of the line image portion changed to blue, the recording material was promptly immersed in ice water. As a result, a color image composed of a white background portion and a blue line image portion was obtained.

As previously explained, the cholesteryl compound of the present invention is a liquid crystalline compound, which can solve the problem of being unable to produce a red color image in the conventional rewritable full-color thermosensitive recording material. Namely, there can be obtained a thermosensitive recording material capable of reproducing iridescent colors selected from the whole visible region by employing the above-mentioned cholesteryl compound of the present invention.

According to the present invention, rewritable full-color recording can be achieved. Therefore, a full-color photograph can be recorded on the thermosensitive recording material of the present invention in the form of a card, and freely changed. Further, when such a full-color thermosensitive recording material is used as a sheet for an overhead projector (OHP), full-color images can be recorded and erased repeatedly. This is considered to be advantageous from the environmental viewpoint.

Japanese Patent Application No. 10-217596 filed Jul. 31, 1998 is hereby incorporated by reference.

What is claimed is:

1. A cholesteryl compound of formula (1):

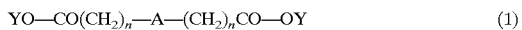

YO—CO(CH$_2$)$_n$—A—(CH$_2$)$_n$CO—OY (1)

wherein A is a 1,5-hexadienylene group represented by the formula —C(R)=CHCH$_2$CH$_2$CH=C(R)—, in which R is a hydrogen atom or methyl group; Y is a cholesterol residue obtained by removing a hydroxyl group from cholesterol; and n is an integer of 5 to 7.

2. A rewritable full-color thermosensitive recording material comprising a cholesteryl compound of formula (1):

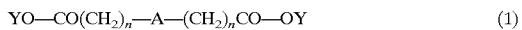

YO—CO(CH$_2$)$_n$—A—(CH$_2$)$_n$CO—OY (1)

wherein A is 1,5-hexadienylene group represented by the formula —C(R)=CHCH$_2$CH$_2$CH=C(R)—, in which R is a hydrogen atom or methyl group; Y is a cholesterol residue obtained by removing a hydroxyl group from cholesterol; and n is an integer of 5 to 7.

* * * * *

UNITED STATES PATENT AND TRADEMARK OFFICE
CERTIFICATE OF CORRECTION

PATENT NO. : 6,183,666 B1
DATED : February 6, 2001
INVENTOR(S) : Nobuyuki Tamaoki, et al.

It is certified that error appears in the above-identified patent and that said Letters Patent is hereby corrected as shown below:

Column 2,
Line 34, "j." should read -- J. --.

Column 4,
Line 21, "Dicholesteryl" should read -- dicholesteryl --.
Line 25, delete item [the] in its entirety.

Signed and Sealed this

Twenty-fifth Day of September, 2001

Attest:

NICHOLAS P. GODICI
Attesting Officer   Acting Director of the United States Patent and Trademark Office